United States Patent [19]

Asai et al.

[11] 4,261,806

[45] Apr. 14, 1981

[54] METHOD FOR THE TREATMENT OF INNER SURFACES OF A TUBULAR BODY OF A PLASTIC WITH LOW TEMPERATURE PLASMA

[75] Inventors: Michihiko Asai, Fujisawa; Yoshio Suda, Hachioji; Kiyoshi Imada, Omiya; Susumu Ueno; Hirokazu Nomura, both of Ibaragi, all of Japan

[73] Assignees: Agency of Industrial Science & Technology; Shin-Etsu Chemical Co. Ltd., both of Tokyo, Japan

[21] Appl. No.: 112,194

[22] Filed: Jan. 15, 1980

[30] Foreign Application Priority Data

Jan. 22, 1979 [JP] Japan .................... 54-6704

[51] Int. Cl.³ .......................... B01K 1/00; B05D 3/06
[52] U.S. Cl. .................... 204/165; 204/168; 250/531; 427/40
[58] Field of Search ............. 204/165, 168, 169, 176; 250/531; 427/40

[56] References Cited

U.S. PATENT DOCUMENTS

| | | | |
|---|---|---|---|
| 3,280,018 | 10/1966 | Denis | 204/164 |
| 3,399,252 | 8/1968 | Hough et al. | 204/165 X |
| 3,497,438 | 2/1970 | Burleson et al. | 204/168 |
| 3,547,802 | 12/1970 | Gleit et al. | 250/531 |
| 3,762,941 | 10/1973 | Hou | 204/168 X |

FOREIGN PATENT DOCUMENTS 925470 5/1973 Canada ........................ 204/168

*Primary Examiner*—F. C. Edmundson
*Attorney, Agent, or Firm*—Toren, McGeady and Stanger

[57] ABSTRACT

The invention provides an effective method for subjecting the inner surface of a tubular body made of a plastic resin to a treatment with low temperature plasma according to which the tubular body is dipped in an insulating oil bath while the inside of the tubular body is filled with a plasma gas under a reduced pressure and electric power for the generation of a low temperature plasma is supplied to electrodes surrounding the tubular body in the insulating oil. Several of the problems in the prior art methods can be solved by the present invention such as undesirable thermal degradation of the tube surface by the evolved by the electric discharge, and power loss due to the generation of plasma outside the tubular body. When the method of the invention is applied to the treatment of a continuous length tubular body, the tubular body is continuously moved in the insulating oil through the electrodes surrounding it, with the optional provision of a sleeve made of an insulating material placed between the electrodes and the tubular body, so as that the tubular body is free from adverse effects caused by direct contact with the electrodes.

5 Claims, 5 Drawing Figures

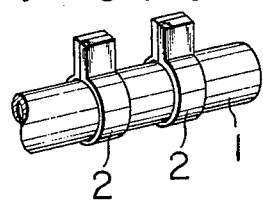
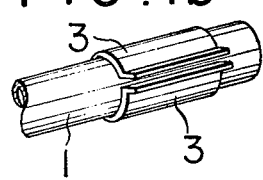
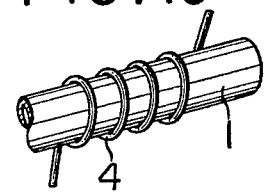
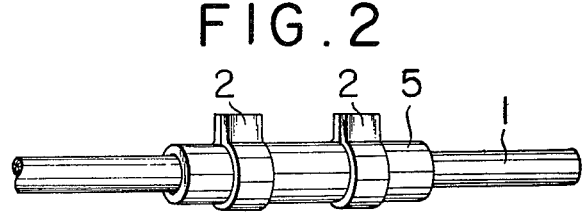
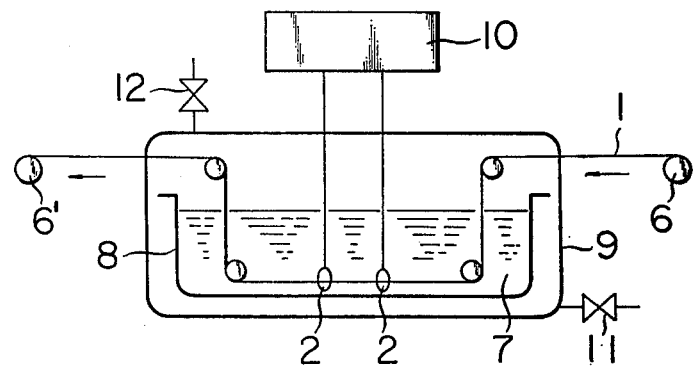

METHOD FOR THE TREATMENT OF INNER SURFACES OF A TUBULAR BODY OF A PLASTIC WITH LOW TEMPERATURE PLASMA

BACKGROUND OF THE INVENTION

The present invention relates to a method for the treatment of inner surfaces of a tubular body made of a plastic with low temperature plasma with an object to improve or modify the properties of the surface.

It has been established that the surface properties of shaped articles made of a synthetic plastic resin can be improved or modified when the surface of the article is treated with or exposed to an atmosphere of low temperature plasma with or without deposition of a polymeric substance formed by the plasma. The surface properties improved or modified by the plasma treatment include, for example, affinity with water, printability, adhesivity, anti-electrostatic property and the like as well as the resistance against bleeding or blooming of the plasticizer and other additives contained in the plastic resin on the surface of the shaped article.

The above described effects obtained by the plasma treatment are considerably or sufficiently remarkable but the applicability of the technique of plasma treatment is limited to the outwardly exposed surfaces of shaped articles such as the outer surfaces of sheets, films, rods, tubes, bottles and other irregular forms. For example, the prior art technique of the plasma treatment can hardly be applied to the inner surfaces of hollow bodies such as tubes. This is because no convenient and reliable method was known hitherto for generating stable low temperature plasma in such a confined space surrounded by the plastic walls.

On the other hand, there is a growing demand for the technique of treating inner surfaces of hollow bodies, e.g. tubes, with low temperature plasma. For instance, the tubes and hoses used in the fields of medical technologies and food industries such as the tubes for transfusion of blood and other therapeutic fluids or hoses for transportation of beverages and edible fats or oils as well as many other tubes or hoses for industrial uses must be absolutely free from migration or bleeding of the plasticizer and other additives toward the inner surface thereof. In addition, many tubular bodies used with a medical purpose as embedded in or in contact with the living tissues of human body such as catheters, artificial vascular tracts, artificial esophagi and the like are desired to have improved adaptability to living body, e.g. antithrombosis and adaptability to tissues.

Therefore, development of a convenient and reliable technique for the continuous treatment of inner surfaces of tubular bodies with low temperature plasma is a very urgent problem in the field of plastics processing.

SUMMARY OF THE INVENTION

It is therefore an object of the present invention to provide a novel and improved method for the continuous treatment of inner surfaces of hollow bodies, e.g. tubes, with low temperature plasma.

The method of the present invention established as a result of the extensive investigations undertaken by the inventors on the above problem comprises dipping the tube in an insulating oil, the inside of the tube being filled with a gas at a pressure suitable for the generation of low temperature plasma, and generating low temperature plasma inside the tube by applying a high frequency voltage to an electrode placed outside the tube.

BRIEF DESCRIPTION OF THE DRAWING

FIGS. 1(a)-1(c) illustrate several modifications of the electrodes wherein:
 FIG. 1(a) shows a pair of ring-like electrodes;
 FIG. 1(b) shows a pair of plate-like electrodes which conform to the curvature of the tube; and
 FIG. 1(c) shows a coiled electrode for inductively coupling to the tube.
 FIG. 2 illustrates an electrode assembly in which an insulating sleeve is surrounded by a pair of ring-like electrodes and the tube passes through the sleeve.
 FIG. 3 is a schematic cross sectional view of an apparatus for practicing the inventive method.

DETAILED DESCRIPTION OF THE PREFERRED EMBODIMENTS

The plastic resins of which the tubes treated by the inventive method include plasticized and unplasticized polyvinyl chloride resins, polyethylenes, polypropylenes and any other synthetic resins as well as certain rubbery elastomers with a limitation that the synthetic polymer is not affected by the insulating oil in which the tube is dipped during the plasma treatment. The wall thickness of the tube is not particularly limitative to the applicability of the inventive method. The tube may be of a continuous length or cut in individual product lengths according to need.

The insulating oil used in the inventive method, in which the tubular body is dipped, should have sufficient electric insulation and stability in plasma discharge. Particularly recommended oils are silicone fluids, fluorocarbon fluids, high-tension insulating oils and the like.

The gas with which the inside of the tubular body is filled during the plasma treatment may be inorganic or organic and the inorganic gases are exemplified by helium, neon, argon, nitrogen, nitrous oxide, nitrogen dioxide, oxygen, air, carbon monoxide, carbon dioxide, hydrogen, chlorine, hydrogen chloride, bromine cyanide, sulfur dioxide, hydrogen sulfide and the like; while the organic gases are exemplified by acetylene, pyridine, gases of organosilane compounds and organopolysiloxane compounds, fluorocarbon compounds and the like. These gases may be used either singly or as a mixture of two kinds or more according to need.

Inorganic gases are used when the object of the plasma treatment is the formation of crosslinks in the surface layer or improvement of the wettability of the surface of the inner walls of tubes or hoses, and organic gases are recommended when the improvement of the adaptability to a living body such as anti-thrombosis is desired, owing to the possibility of deposition of certain polymerized matter on the surface.

Low temperature plasma is mainly produced by glow discharge in a gaseous atmosphere of a pressure in the range from 0.001 to 10 Torr or, preferably, in the range from 0.01 to 1 Torr where the frequency of the electric power supply for the discharge is not limitative ranging from direct current to the microwave region. In particular, a frequency of the so-called high frequency region is recommended due to the possibility of obtaining stable plasma discharge. For example, a frequency of 13.56 MHz or 27.12 MHz is recommended since these frequencies are relatively free from statutory regulations for radio waves.

The shapes and arrangements of the electrodes for the power supply are not particularly limitative in so far as a stable plasma discharge is obtained inside the tubular body. For example, a pair of plate-like electrodes, a pair of ring-like electrodes, a single coiled electrode and the like may be used. Electrodes of the former two types are connected to the high-frequency generator by capacitive coupling and the coiled electrodes are used by inductive coupling. Several examples of the electrode configurations are illustrated in FIG. 1(2), FIG. 1(b) and FIG. 1(c). FIG. 1(a) shows a pair of bandage-like or ring-like electrodes 2, 2 arranged in the axial direction of the tubular body 1 surrounded by each of the electrodes 2, 2. FIG. 1(b) shows a pair of plate-like electrodes 3, 3 each curved along the outer circumference of the tubular body 1 which passes through the space formed by the paired electrodes 3, 3. FIG. 1(c) shows a single electrode 4 of several turns surrounding the tubular body 1, the latter thus passing through the electrode 4. The material for these electrodes is usually a metal having good electric conductivity such as copper and aluminium. It is optional that these electrodes be provided with an insulating layer of inorganic or organic materials on the surface thereof.

The tubular body may be in direct contact with the electrodes as is the case in FIGS. 1(a) to (c) without particular drawbacks. It is, however, sometimes advantageous that, as is illustrated in FIG. 2, the electrodes 2, 2 surround a sleeve 5 made of an insulating material such as glass and the tubular body 1 passes through the sleeve 5. In this arrangement of the electrodes and the sleeve, any undesirable effect caused by the local heating the tubular body by the electrodes, or by rubbing of the tubular body with the electrodes can be avoided.

FIG. 3 is a schematic illustration of the procedure for practicing the inventive method. In the figure, the continuous length tube 1 wound around the reel 6 is wound up by the reel 6' continuously at a suitable speed as supported by the guide pulleys. On the path of travel of the tube 1 from the first reel 6 to the second reel 6', the tube 1 passes through a pair of ring-like electrodes 2, 2 which are immersed in a bath 7 of an insulating oil contained in a vessel 8. The ends of the tube 1 are connected to a gas supply system or an evacuation means through the hollow shafts of the reels 6 and 6', respectively, so that the inside of the tube 1 is filled with a desired plasma gas under pressure as mentioned before.

On the other hand, the electrodes 2, 2 are each connected to the terminals of a high frequency power supply 10 and low temperature plasma is generated inside the tube 1 by supplying a high frequency electric power to the electrodes 2, 2 while the tube 1 is continuously running through the electrodes 2, 2 to effect the plasma treatment of the inner surface of the tube 1.

The vessel 8 may be placed in an open atmosphere and the procedure can be performed under atmospheric pressure. It should be noted, however, that the tube 1 sometimes collapses by the pressure difference between inside and outside of the tube 1 when under atmospheric pressure, especially, with a relatively small thickness of the wall of the tube 1. In such a case, the box 9 in which the vessel 8 is placed is evacuated by connecting the valve 11 to a vacuum pump (not shown in the figure) with the valve 12 closed so that the pressures inside and outside the tube 1 can be balanced.

The insulating oil 7 contained in the vessel 8 is more or less subject to temperature elevation by the heat evolved in the plasma discharge so that it is sometimes desirable that a cooling means is installed to cool the insulating oil 7, for example, by circulating a cooling medium.

The advantages obtained by the inventive method over conventional methods for plasma treatment where no insulating oil is used will be more apparent from the discussions below.

Firstly, when the procedure of plasma treatment of a tubular body is carried out in an atmospheric air without the use of an insulating oil as in the present invention, a large quantity of heat is produced at the electrodes in order to generate low temperature plasma inside the tubular body under a reduced pressure with a sufficient intensity so that the outer surface of the plastic tube undergoes thermal deterioration or is damaged by the heat at the positions near the electrodes. For example, a tubular body made of a plastic having a relatively low softening point such as a plasticized polyvinyl chloride resin is readily denaturated with discoloration or deformed by the heat at the areas in contact with the electrodes necessitating a cooling means for the electrodes. In this connection, the inventive method provides an effective cooling means for the electrodes as well as the tubular body under treatment by the insulating oil in which the electrodes and the tubular body are immersed.

Secondly, the inventive method gives a possibility of enhancing the power efficiency of the plasma discharge with the electrodes and the tubular body immersed in an insulating oil. When the external pressure of the tubular body is reduced to balance with the pressure inside the tubular body in order to prevent collapsing of the tubular body by the pressure difference, low temperature plasma is generated not only in the inside of the tubular body but also in the outer regions of the tubular body around the electrodes, where the pressure is also reduced to such an extent suitable for plasma discharge resulting in a large loss of the electric power. Contrary to the above case without the use of an insulating oil, the inventive method prevents the plasma discharge in the regions outside the tubular body since the electrodes and the tubular body under treatment are dipped in an insulating oil which may be under a reduced pressure in the box as is described above. Consequently, low temperature plasma is generated only inside the tubular body with full utilization of the electric power.

Thirdly, the insulating oil also has a lubricating effect so that the undesirable effects caused by the frictional contact or rubbing between the outer surface of the tubular body and the electrodes or the sleeve can be reduced even when the tubular body is running within the electrodes or through the sleeve in contact therewith. Accordingly, continuous process for the plasma treatment of a continuous length tubular body is greatly facilitated.

Following are the examples to illustrate the inventive method in further detail.

EXAMPLE 1.

A continuous length tube of a plasticized polyvinyl chloride resin having an inner diameter of 10 mm and a wall thickness of 2 mm was prepared by extrusion-molding a compound composed of 100 parts by weight of a polyvinyl chloride resin (TK-1300, a product by Shin-Estu Chemical Co., Japan) 50 parts by weight of dioctyl phthalate, 1.5 parts by weight of calcium stearate and 1.5 parts by weight of zinc stearate. The plasma treatment of the above prepared tube was undertaken with the apparatus depicted in FIG. 3.

The pressure inside the box 9 was maintained at 1.0 Torr while the pressure inside the tube 1 was maintained at 0.5 Torr by passing carbon monoxide gas under a reduced pressure. The insulating oil 7 was a dimethyl silicone fluid having a viscosity of about 300 centistokes at 25° C. (KF 96, a product by Shin-Etsu Chemical Co.).

A high frequency power of 300 watts with a frequency of 13.56 MHz was supplied to the ring-like electrodes placed 10 cm apart from each other surrounding the tube to generate low temperature plasma inside the tube which was traveling at a velocity of 10 cm/minute pulled by the reel.

A 15 cm long portion cut from the continuous length tube after the plasma treatment was filled with n-hexane with its two open ends stoppered and kept at 37° C. in a thermostat for 2 hours. The amount of dioctyl phthalate leached out of the tube into the n-hexane was 0.8 mg. A comparative test undertaken with an untreated tube gave a result that the amount of dioctyl phthalate leached out into n-hexane was 37 mg.

In order to examine the wettability of the inner tube surface with water, the plasma-treated and untreated tubes above described were cut open and the contact angles of water on their surfaces were determined to find that the angle for the plasma-treated tube was 27° while the angle for the untreated tube was 90°.

For comparison, the procedure of plasma treatment was repeated with the same conditions as described above excepting the omission of the insulating oil. In this case, the temperature of the electrodes was elevated considerably by the heat of plasma discharge so that the outer surface of the tube become softened and deformed with difficulties in continuous running of the procedure.

EXAMPLE 2.

A continuous length tube having an inner diameter of 10 mm and a wall thickness of 3 mm was prepared with a molding compound composed of 100 parts by weight of a polyvinyl chloride resin (TK-1300), 30 parts by weight of dioctyl phthalate, 3 parts by weight of an epoxy resin (Epikote 815, a product by Shell Chemical Co.), 1.5 parts by weight of calcium stearate and 1.5 parts by weight of zinc stearate and the inner surface of the tube was subjected to the treatment with low temperature plasma in an apparatus shown in FIG. 3.

In this case, the atmosphere surrounding the insulating oil was open to the atmospheric air by opening the valves and the inside of the tube was filled with a 15:85 by volume mixed gas of carbon monoxide and argon under a pressure of 1.0 Torr. The insulating oil was a methylphenylsilicone fluid having a viscosity of about 450 centistokes at 25° C. (KT 54, a product by Shin-Etsu Chemical Co.).

A high frequency electric power of 500 watts with a frequency of 13.56 MHz was supplied to the ring-like electrodes in the insulating oil placed 15 cm apart from each other to generate low temperature plasma inside the tube traveling through the electrodes at a velocity of 15 cm/minute continuously.

The leaching test of dioctyl phthalate into n-hexane and the measurement of the contact angle of water on the surface were performed with the plasma-treated and untreated tubes in the same manner as in Example 1 to give the results below.

|  | Amount of dioctyl phthalate, mg | Contact angle of water |
|---|---|---|
| Plasma-treated | 0.5 | 34° |
| Untreated | 22 | 90° |

For comparison, a trial was made to carry out the plasma treatment of the same tube with the same conditions as above but without the use of the insulating oil. In this case, the tube was markedly softened by the heat of discharge so that the tube collapsed by the pressure difference between the inside and outside of the tube resulting in interruption of the treatment.

EXAMPLE 3

A continuous length tube having an inner diameter of 10 mm and a wall thickness of 2 mm was prepared with a molding compound composed of 100 parts by weight of a polyvinyl chloride resin (TK-1300), 25 parts by weight of dioctyl phthalate, 15 parts by weight of a urethane elastomer (T-1070, a product by Takeda Pharmaceutical Industry Co., Japan), 1.5 parts by weight of calcium stearate and 1.5 parts by weight of zinc stearate and the inner surface of the tube was subjected to the treatment with low temperature plasma in an apparatus shown in FIG. 3.

In this case, the atmosphere surrounding the insulating oil was open to the atmospheric air by opening the valves and the inside of the tube was filled with carbon monoxide gas under a pressure of 0.3 Torr. The insulating oil was a high-tension insulating oil manufactured by Nippon Petroleum Co., Japan.

A high frequency electric power of 200 watts with a frequency of 13.56 MHz was supplied to the ring-like electrodes in the insulating oil placed 7 cm apart from each other to generate low temperature plasma inside the tube traveling through the electrodes at a velocity of 3 cm/minute continuously.

The leaching test of dioctyl phthalate into n-hexane and the measurement of the contact angle of water on the surface were performed with the plasma-treated and untreated tubes in the same manner as in Example 1 to give the results below.

|  | Amount of dioctyl phthalate, mg | Contact angle of water |
|---|---|---|
| Plasma-treated | 0.3 | 30° |
| Untreated | 15 | 90° |

EXAMPLE 4.

The experimental procedure was substantially the same as in Example 1 excepting that the pressure inside the tube was maintained at 0.4 Torr by passing a 12.5:87.5 by volume mixed gas of carbon monoxide and argon instead of 0.5 Torr with carbon monoxide gas, the high frequency electric power supply was 400 watts instead of 300 watts and the traveling velocity of the tube was 3 cm/minute instead of 10 cm/minute (Experiment No. 4-1).

In the second experiment, a glass sleeve having an inner diameter of 15 mm was used as surrounded by the ring-like electrodes and the tube was passed through the sleeve, the other conditions being the same as in Experiment No. 4-1 above (Experiment No. 4-2).

In the third experiment, the ring-like electrodes used in Experiment No. 4-1 were replaced with a coiled electrode having a distance of 10 cm between its terminals, the other conditions being the same as in Experiment No. 4-1 (Experiment No. 4-3).

The thus plasma-treated tubes obtained in Experiments No. 4-1, No. 4-2 and No. 4-3 were examined for the leaching of dioctyl phthalate into n-hexane in the same manner as in Example 1 to give the results of 0.3 mg, 0.5 mg and 0.8 mg, respectively. The contact angle of water on the surface of each of the thus plasma-treated tubes was 23°.

EXAMPLE 5

A high-density polyethylene tube having an inner diameter of 10 mm and a wall thickness of 1 mm was subjected to the plasma-treatment of its inner surface in the apparatus shown in FIG. 3 with the valves of the box open to the atmospheric air. The pressure inside the tube was maintained at 0.2 Torr by passing a 1:1 by volume mixed gas of hexamethyldisiloxane and argon. The insulating oil was the same methylphenylsilicone fluid as used in Example 2.

A high frequency electric power of 100 watts with a frequency of 13.56 MHz was supplied to the ring-like electrodes in the insulating oil placed 10 cm apart from each other to generate low temperature plasma inside the tube traveling through the electrodes at a velocity of 3 cm/minute. The thus plasma-treated tube was cut open and examined to find that the inner surface was coated with a thin film of a silicon-containing polymeric substance having a thickness of about 0.05 μm deposited thereon.

The plasma-treated and untreated polyethylene tubes were subjected in parallel to the Lee-White test for anti-thrombosis. Thus, 1 ml of fresh human blood was introduced into a 10 cm portion cut from each of the tubes and closed at one end after washing with physiological saline solution at 60° C. and the tubes were tilted back and forth every 30 to 60 seconds to move the blood in the tubes until the blood had lost flowability.

The time of blood coagulation determined in this manner was 10 minutes for the untreated tube while the time was 30 minutes for the plasma-treated tube indicating the remarkable effectiveness of the inventive method for the improvement of anti-thrombosis.

What is claimed is:

1. A method for treating the inner surface of a tubular body made of a plastic resin comprising the steps of filling the interior of the tubular body with a gas at a reduced pressure sufficient to generate a low temperature plasma to treat the inner surface of the tubular body when the gas is subjected to electromagnetic energy, arranging a bath of insulating oil and dipping the tubular body in the bath of insulating oil, surrounding the tubular body in the oil bath with at least one electrode, and supplying electromagnetic energy to the electrode to generate the low temperature plasma in the gas inside the tubular body.

2. A method for treating the inner surface of a tubular body made of a plastic resin comprising the steps of filling the interior of the tubular body with a gas at a reduced pressure sufficient to generate a low temperature plasma to treat the inner surface of the tubular body when the gas is subjected to electromagnetic energy, arranging a bath of insulating oil and dipping the tubular body in the insulating oil, surrounding the tubular body in the oil bath with a sleeve made of insulating material, surrounding the sleeve with at least one electrode, and supplying electromagnetic energy to the electrode to generate the low temperature plasma in the gas inside the tubular body.

3. The method as claimed in claims 1 or 2, including dipping the tubular body in a bath of insulating oil comprising silicone fluid.

4. The method as claimed in claim 1 or 2, including filling the interior of the tubular body with a gas at a pressure in the range of from 0.001 to 10 Torr.

5. The method as claimed in claim 1 or 2, including continuously moving the tubular body through the electrode in the oil bath.

* * * * *